(12) United States Patent
Richter et al.

(10) Patent No.: US 11,399,978 B2
(45) Date of Patent: Aug. 2, 2022

(54) FREE JET DOSAGE SYSTEM FOR THE EYE

(71) Applicant: Fraunhofer-Gesellschaft zur Foerderung der angewandten Forschung e.V., Munich (DE)

(72) Inventors: Martin Richter, Munich (DE); Axel Wille, Germering (DE); Christian Wald, Munich (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 885 days.

(21) Appl. No.: 15/373,232

(22) Filed: Dec. 8, 2016

(65) Prior Publication Data

US 2017/0156927 A1 Jun. 8, 2017

(30) Foreign Application Priority Data

Dec. 8, 2015 (DE) ...................... 10 2015 224 617.5

(51) Int. Cl.
*A61F 9/00* (2006.01)
*A61M 11/00* (2006.01)
*A61M 11/06* (2006.01)

(52) U.S. Cl.
CPC .......... *A61F 9/0026* (2013.01); *A61F 9/0008* (2013.01); *A61M 11/005* (2013.01); *A61M 11/065* (2014.02); *A61F 2009/0043* (2013.01); *A61M 2205/3306* (2013.01); *A61M 2205/3375* (2013.01); *A61M 2205/52* (2013.01);

(Continued)

(58) Field of Classification Search
CPC ........ A61F 9/0026; A61F 9/0008; A61F 9/00; A61F 2009/0043; A61M 11/005; A61M 11/065; A61M 2210/0612; A61M 2230/63; A61M 2230/005; A61M 2205/52; A61M 2205/3375; A61M 2205/3306; A61M 31/00; G02C 11/00; A61J 1/1443; B65D 47/18; B05B 17/06
See application file for complete search history.

(56) References Cited

U.S. PATENT DOCUMENTS 6,253,605 B1 * 7/2001 Richter .................. G01F 1/363
73/203
9,039,666 B2 * 5/2015 Voss ..................... A61M 11/007
604/290

(Continued)

FOREIGN PATENT DOCUMENTS

DE 19616300 A1 10/1997
DE 10220371 A1 11/2003
(Continued)

*Primary Examiner* — Ariana Zimbouski
*Assistant Examiner* — Gabriella E Burnette
(74) *Attorney, Agent, or Firm* — Perkins Coie LLP; Michael A. Glenn

(57) ABSTRACT

A free jet dosage system serves for administering a fluid into an eye. The free jet dosage system includes a micropump having an inlet and an outlet, the micropump being configured to transfer the fluid from the inlet to the outlet and to dispense the fluid at the outlet to the eye as a free jet. The free jet dosage system further includes a sensor configured to sense the eye and to controller a control, and a micropump, wherein the controller is configured to activate the micropump as soon as the eye is sensed by the sensor.

17 Claims, 7 Drawing Sheets

(52) U.S. Cl.
CPC .............. *A61M 2210/0612* (2013.01); *A61M 2230/005* (2013.01); *A61M 2230/63* (2013.01)

(56) References Cited

U.S. PATENT DOCUMENTS

| | | | |
|---|---|---|---|
| 9,939,730 B2* | 4/2018 | Pauls | G03F 7/7085 |
| 2004/0039355 A1* | 2/2004 | Gonzalez | A61M 15/008 |
| | | | 604/298 |
| 2004/0204674 A1* | 10/2004 | Anderson | A61M 5/1723 |
| | | | 604/66 |
| 2007/0211212 A1* | 9/2007 | Bennwik | A61F 9/0008 |
| | | | 351/221 |
| 2009/0245639 A1* | 10/2009 | Erdler | G06T 5/20 |
| | | | 382/173 |
| 2010/0057060 A1* | 3/2010 | Herekar | A61F 9/008 |
| | | | 606/4 |
| 2011/0106025 A1* | 5/2011 | Hall | A61B 5/1103 |
| | | | 604/298 |
| 2011/0142688 A1* | 6/2011 | Chappel | F04B 43/043 |
| | | | 417/213 |
| 2013/0183209 A1* | 7/2013 | Richter | A61M 5/16877 |
| | | | 422/403 |
| 2014/0187969 A1* | 7/2014 | Hunter | A61B 5/1103 |
| | | | 600/476 |
| 2016/0354240 A1* | 12/2016 | Chauhan | A61F 9/0008 |
| 2017/0156927 A1* | 6/2017 | Richter | A61F 9/0026 |
| 2017/0157329 A1* | 6/2017 | Richter | A61K 9/0021 |
| 2017/0160113 A1* | 6/2017 | Richter | F04B 23/028 |

FOREIGN PATENT DOCUMENTS

| | | |
|---|---|---|
| DE | 202009015776 U1 | 5/2010 |
| EP | 1488106 B1 | 6/2006 |
| WO | 03095837 A1 | 11/2003 |

* cited by examiner

FREE JET DOSAGE SYSTEM FOR THE EYE

CROSS-REFERENCE TO RELATED APPLICATIONS

This application claims priority from German Patent Application No. 102015224617.5, which was filed on Dec. 8, 2015, and is incorporated herein in its entirety by reference.

BACKGROUND OF THE INVENTION

Embodiments of the present invention relate to a free jet dosage system for administering a fluid to an eye, to an eye drops bottle comprising a free jet dosage system and to a pair of glasses comprising a free jet dosage system arranged in the frame thereof. Further embodiments relate to the use of a micro dosage pump for administering ophthalmic medication.

The free jet dosage system serves for dispensing fluids or liquids into the eye, e.g., for treating glaucoma patients.

In Germany alone, there are 1.4 m patients having to take eye drops several times a day. With a bottle per month and patient, the market potential in Germany alone is enormous and amounts to around 16.8 m units per year.

In the treatment of glaucoma using conventional eye drops or, generally speaking, conventional dosage systems, problems often arise related to the dosage accuracy and the application of the medication itself, which suffers from lack of compliance (participation) or simply from the inability of the patients (due to tremor or trembling). Further problems and possibilities for improvement arise with regard to monitoring the dispensing of the medication. Currently, the physician may only check this indirectly, e.g., by judging the improvement or deterioration of the patients' eyes.

Some known approaches have already tried to solve the addressed deficiencies, however, there is still no comprehensive approach.

Thus, on the one hand, conventional devices with improved ergonomics are known, e.g., small eye drops bottles comprising funnels that may be put onto the eye, or dosage aids such as Autodrop—an aid for the eye drop application—which includes a plastic funnel to be placed onto the eye socket comprising an insert for the drops bottle. In such funnels, e.g., a small observation slit causes the patient to look up during the eye drop application so that the eye is directed away from the falling drop.

Also, some technological approaches are known such as the free jet dispenser of Patent Application No. DE 10 220 371 A1 or EP 1 488 106 B1, respectively. In that regard, patent DE 19 616 300 A1 is to be noted, which shows a method and a device for the non-contact application of liquids of diagnostic or therapeutic pharmaceutics at the human eye. However, none of these approaches provides a solution for excluding the above-mentioned incorrect operations. Hence, there is a need for an improved approach.

SUMMARY

According to an embodiment, a free jet dosage system for administering a fluid into an eye may have: a micropump having an inlet and an outlet, the micropump being configured to transfer the fluid from the inlet to the outlet and to dispense the fluid at the outlet to the eye as a free jet; a sensor configured to sense the eye; and a controller for controlling the micropump configured to activate the micropump as soon as the eye is sensed by the sensor.

Another embodiment may have an eye drops bottle having an inventive free jet dosage system.

Another embodiment may have a pair of glasses having an inventive free jet dosage system which is arranged in the frame of the glasses.

According to another embodiment, a method for administering a fluid into an eye may have the steps of: sensing an eye by means of a sensor; and activating a micropump as soon as the eye is sensed by the sensor so that, on the outlet side, a fluid is dispensed to the eye by means of the micropump as a free jet.

Another embodiment may have a usage of a micropump for administering an ophthalmic medication in the form of a free jet into an eye, the micropump having an inlet and an outlet, an wherein the micropump is configured to transfer the ophthalmic medication from the inlet to the outlet and to dispense the ophthalmic medication at the outlet to the eye as a free jet.

Embodiments of the present invention provide a free jet dosage system for administering a fluid such as an ophthalmic medication for the treatment of glaucoma or, generally speaking, eye drops into an eye. The free jet dosage system includes a micropump, a sensor and a controller. The micropump comprises an inlet and an outlet, and is configured to transfer the fluid from the inlet to the outlet and to dispense the fluid at the outlet as a free jet to the eye. The sensor is configured to sense the eye. The micropump is controlled by the controller such that the micropump is activated as soon as the eye is sensed by the sensor.

Hence, it is the essence of the present invention that a medication dosage is enabled by the device, or rather the dosage system, by using a "free jet" dispensed in a sensor-controlled way. Here, the sensor identifies the eye and, having identified the eye, controls a pump for creating a jet that is aligned in relation to the sensor such that it hits the identified eye. In this way, the medication may be safely applied to the eye, ruling out an incorrect dosage due to blinking or missing the eye. Further, it is possible to set the dosed amount with sufficient accuracy since the dosed amount does not depend anymore on gravity acting on the drop. It is a further advantage that the ergonomics of such a system are substantially improved compared to conventional eye drops so that administering the eye drops is still also possible for older patients. Generally, this helps to promote the acceptance among the patients.

The sensor identifying the eye may be implemented in different ways. According to a first embodiment, a simple reflection optics is used as sensor, which is configured to determine a reflectance of a surface on which the reflection optics is directed. The reflectance may be used to identify if the sensor is directed on an eye or on another surface. According to embodiments, the reflection optics at least comprises a photodiode and a light source. According to further embodiments, as an alternative to the reflection optics, an ultrasonic sensor for determining the distance or a different sensor such as a CCD-sensor of a camera may be used. By using a camera it is also not only possible to identify when an eye is present and/or if the same is open or closed, but also if it is a left or a right eye.

In general, according to further embodiments, both the sensor in the form of a camera and the sensor in the form of reflection optics are configured to identify blinking. Blinking allows for a conclusion as to whether administering the fluid into the eye was successful. This allows for a feedback function for the patient. Further, according to embodiments, the successful administration or the administration in general may be stored in a memory of the free jet dosage system, the memory being readable through its optional interface, e.g., by an ophthalmologist. Due to this logging, the physician may for the first time monitor the therapy by means of the dosage of the medications. From this, it may also be identified if the patient stops or refuses administering the drug so that the worst consequence, i.e., loss of sight (which still occurs in 10% of glaucoma cases), may be prevented.

According to further embodiments, the micropump is configured to administer the fluid in the appropriate amount such as 10 µl or <40 µl or, if necessitated, to repeat the administration to reach the prescribed total amount. With the right selection of micropumps, the administration may also occur several times in succession in such short intervals that no blinking between the individual doses is to be expected.

According to embodiments, the micropump comprises a chamber and a membrane integrated into the chamber, as well as a piezo actuator for moving the membrane.

Further embodiments relate to an eye drops bottle comprising a free jet dosage system according to the above-mentioned specification. Alternatively, according to further embodiments, it would be conceivable that the free jet dosage system is arranged in a pair of glasses or, to be precise, in the frame of the pair of glasses. In this case, a cartridge for the fluid may also be integrated into the pair of glasses, which may also be replaced accordingly.

Further embodiments relate to a method for administering the fluid or the medication. The method includes the following steps: sensing an eye by means of a sensor, activating the micropump as soon as the eye is sensed by the sensor so as to dispense on the outlet side a fluid as a free jet into the eye by means of the micropump. Same as the above-mentioned embodiments, this method has the advantage that not only large-volume drops, which are, e.g., difficult to dose by means of a typical squeeze bottle, but also very small-volume drops may be reliably dispensed in a precisely determined dose.

A further embodiment relates generally to the use of the above-described micro dosage pump for administering ophthalmic medication, e.g., for treating glaucoma or dry eyes.

BRIEF DESCRIPTION OF THE DRAWINGS

Embodiments of the present invention will be detailed subsequently referring to the appended drawings, in which.

DETAILED DESCRIPTION OF THE INVENTION

Figure 1A:
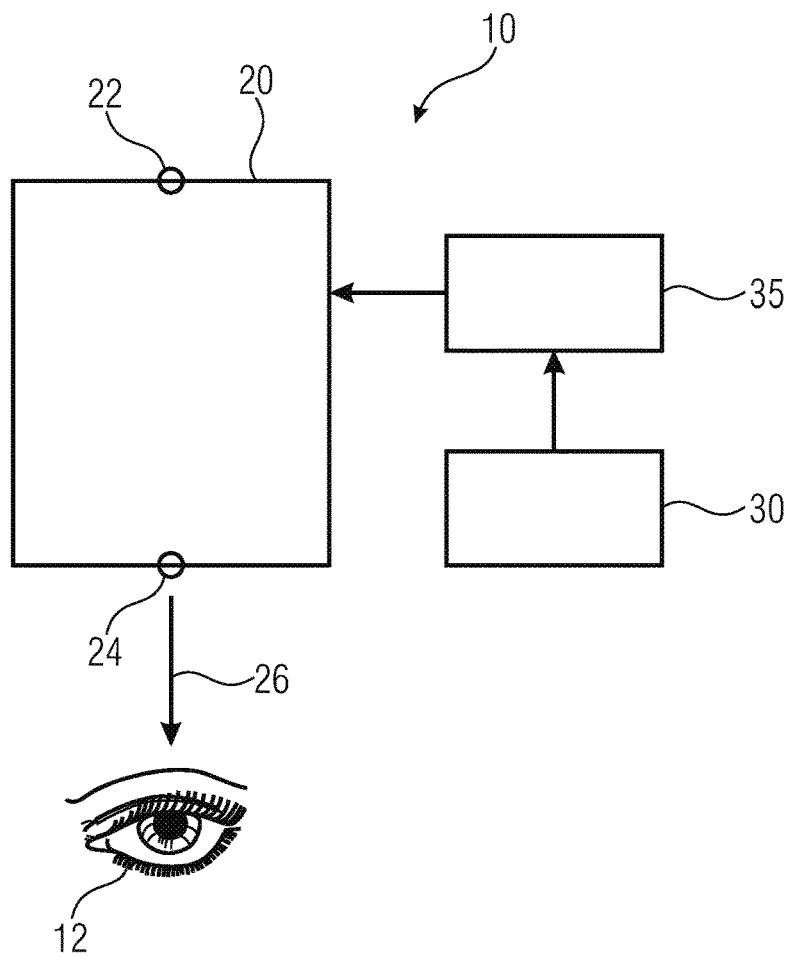
FIG. 1a shows a schematic block diagram of a free jet dosage system according to a basic embodiment.

Before embodiments of the present disclosure are subsequently described in greater detail with reference to the drawings, it should be noted that the same or equivalent elements and steps are denoted by the same reference numerals so that their description is interchangeable.

FIG. 1a shows a free jet dosage system 10 comprising a micropump 20 and a sensor 30, a controller 35 being connected between the sensor 30 and the micropump 20.

The micropump 20 includes an inlet 22 for a fluid and an outlet 24. The micropump 20 is configured to receive the fluid through the inlet 22 or to draw in the fluid at the inlet 22 in order to transfer it to the outlet 24 and to dispense it there as a free jet 26 towards the eye 22. At this point, for the sake of completeness, it is to be noted that the free jet 26 includes the fluid, e.g., a medication (for treating glaucoma), to be dosed into the eye 12. According to the embodiment, in order to reliably create this free jet 26, the outlet 24 may be formed as a nozzle or a (single) diaphragm.

As explained above, it is a problem to dispense the fluid into the eye and not next to eye or onto the eye lid. In order to ensure this, the free jet dosage system 10 comprises the sensor 30 serving for the observation of the eye 12. For example, the sensor 30 may be a camera or reflection optics configured to sense the eye. As soon as the eye is sensed, the micropump 20 is activated by means of the controller 35. Consequently, the fluid or medication is dispensed (dosed) as a free jet into the eye 12 or, generally, in the direction of the eye 12 as soon as the sensor identifies that the free jet nozzle 24 aims at the eye.

Figure 1B:
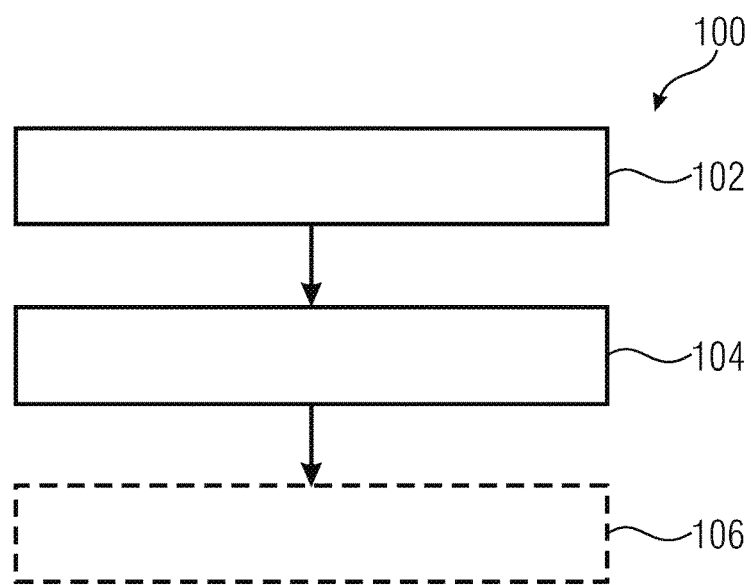
FIG. 1b shows a schematic flow diagram of a method of dosage.

From a different point of view, this means that the free jet dosage system performs the method 100 depicted in FIG. 1b.

At this point, it is to be noted that a free jet 26 substantially differs from conventional gravity drops (cf. eye drops, approx. 40 µl) or a micro dosage drop (cf. ink-jet printer), respectively, in terms of amount and shape. As a general rule, a free jet 26, for example, as used herein, comprises an actual elongated jet shape, e.g., with a length of 1-50 mm and a total amount in the range of 20 nl to 100 nl or from 40 nl to 500 nl; hence, a comparably small amount for a non-compact volume arrangement. Consequently, such amounts at the above-mentioned length lead to a very thin jet thickness, the creating of the free jet 26 being based on the combination of a relatively high stroke volume and a relatively fine nozzle. Compared to a micro dosage drop (ink-jet principle, which comprises a volume of approx. 20 to 100 µl and is essentially round), the volume of the free jet is very large.

FIG. 1b shows the method 100 with the basic steps 102 and 104 as well as the optional step 106. The basic step 102 relates to sensing the eye 12 by means of the sensor 30. The basic step 104 is activating the micropump 20 as soon as the eye 12 is sensed by the sensor 30 so that a fluid may be dispensed as a free jet 26 at the outlet side into the eye 12 by means of the micropump 20. Thus, automatic triggering of the dosage program is enabled, wherein the trigger event may be the presence of an eye, the presence of an open eye but also the presence of the correct eye.

After the step 104, the optional step 106 may follow, according to which a success may be checked. For example, this success assessment 106 is realized by detecting the blinking of an eye, which is inevitable as a result of dispensing a dosage. The background for this is that, when the jet 26 hits into the eye 12, the person blinks involuntarily but with a delay of a few hundredths of a second. This blinking in a determined time interval may be sensed by the sensor system 30 so that a bio-feedback is obtained as to whether the liquid has entered the eye. The possibility of the bio-feedback may also be sorted under the keyword Control-in-the-Loop.

Figure 2A:
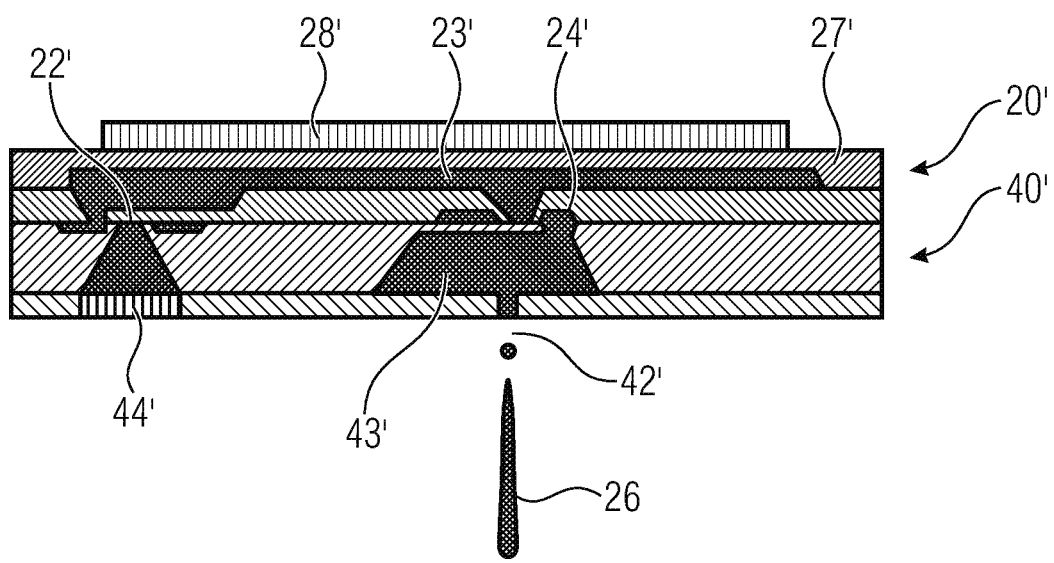
FIG. 2a shows a schematic block diagram of a micropump in the free jet dosage system according to a further embodiment.

Referring to FIG. 2, a micropump is illustrated, which may be applied in the free jet dosage system presented herein. FIG. 2a shows a micropump 20' with an inlet 22', which is embodied herein as an inlet valve, and an outlet 24', which is embodied herein as an outlet valve 24'. A pump chamber 23' is provided between the inlet 22' and the outlet 24'. A membrane 27' is arranged on the side of the pump chamber 23' sealing the pump chamber 23'. The membrane 27' is driven by a piezo actuator 28' extensively arranged on the membrane 27'.

The operation may be described as follows. The fluid is drawn into the pump chamber 23' through the inlet valve 22', which is embodied herein as a one-way valve (realized by a bending bar structure). The pump chamber 23' is now filled with the fluid while the outlet valve 24', which is also embodied as a one-way valve (realized by a bending bar), is held back. Now, if the piezo actuator 28' or, generally speaking, the actuator 28' is driven, a deformation of the membrane 27' occurs so that the volume of the pump chamber 23' is reduced, the pressure on the outlet valve 24' rises and it opens. At this point, it is to be noted that, in response to that, the pressure on the inlet valve 22' also rises, which cannot open due to the one-way characteristic. As a result of opening the outlet valve 24', the fluid is now being dispensed out of the chamber 23'. In a next step, when the actuator 28' is now no longer activated, the membrane 27' moves back into the starting position so that a negative pressure is created in the pump chamber 23', as a result of which fluid is again drawn into the chamber 23' through the inlet valve 22'.

In this embodiment, on the bottom side, on which the inlet and the outlet 22' and 24' are arranged, the micropump 20' is provided with an optional nozzle chip 40'. It includes on the outlet side a nozzle 42', which is embodied as a diaphragm, in combination with a nozzle chamber 43', the nozzle 42' and the nozzle chamber 43' cooperating in such a way that, during a pump activity of the pump chip 20', the free jet 26 is being dispensed. Optionally, the pump chip 20' comprises a filter 44' that is coupled to the inlet valve 22' or overlaps so that the inlet valve 22' above the pump chip 20' may draw in the fluid.

Despite the combination of pump chip 20' and nozzle chip 40', a flat design may be realized. At this point, it is to be noted that such chips are typically etched from silicon or, generally speaking, are manufactured using semiconductor technologies, respectively. Alternatively to the dosage-chip variation made of silicon, it may also include ceramic or glass or be configured of metal layers, e.g., spring stainless steel, which may be fitted onto each other by laser welding or thermal diffusion bonding, for example. This compact design allows for integrating the free jet dosage system, e.g., in a small eye drops bottle. In order to still reach a sufficient dosage amount with such small micropumps, the micropump chip 20' illustrated herein may be operated in a high-frequency manner so that a plurality of strokes (e.g., 1 to 40 µl and/or 10 to 40 µl or even more than 40 µl per stroke) may be realized. In this regard, the stroke sequence may also be chosen to be short enough so that the eyes' reaction time for blinking is longer.

As explained above, the micro dosage chip described herein including the micropump chip 20' and the nozzle chip 40' is self-drawing so that an error-free liquid handling may be ensured.

Figure 2B:
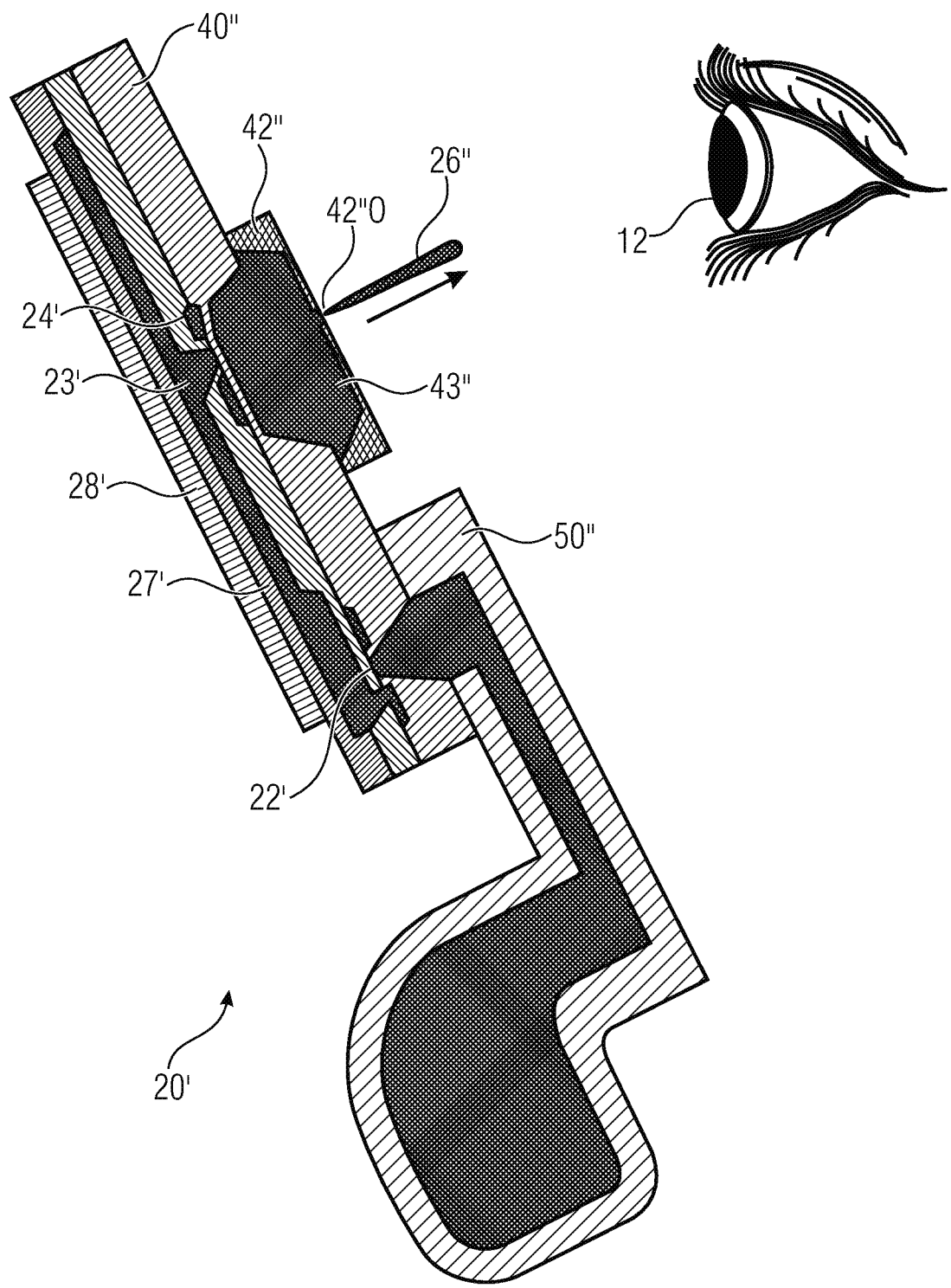
FIG. 2b shows a schematic block diagram of a micropump for the free jet dosage system according to a further embodiment.

FIG. 2b shows another micro dosage chip including the micropump chip 20', the nozzle chip 40", an external nozzle 42" and a reservoir 50".

The micropump chip 20' corresponds to the micropump chip of FIG. 2a. The nozzle chip 40" serves for connecting the micropump chip 20' to the external nozzle chip 42" on the outlet side and for connecting the same to the reservoir 50" on the inlet side.

For example, the reservoir 50' may include a precisely defined volume filled with the fluid, or it may be formed as an interface for a cartridge or a small eye drop bottle, respectively. In this embodiment, the external nozzle 42" is not formed as a simple diaphragm but as an add-on element comprising the opening 42"O so that the volume 43" is formed behind the opening 42"O by the nozzle chip 40" and the nozzle 42".

Compared to the dispensers available on the market, the dosage chip described herein may dose the smallest amounts of liquid, e.g., from the nanoliter range to some 10 µl per second, towards the eye 12 as a free jet 26. In this case, the micropump 20' is not only self-drawing but also bubble-tolerant. This may be realized in that the bubbles are transferred through the pump 20' and transported away during operation. By using the valves 22' and 24', it may be realized that no further air enters the pump chamber 27' so that repeated bubble formation does not occur. In this case, the valve 24' also prevents that dripping does not occur. Also, larger bubbles and/or changing a tube or a medium do not lead to failure. Due to the above mentioned self-drawing capability, operation may rapidly continue even after changing a medium or a tube since the self-drawing capability ensures a reliable operation after a few strokes. The small size is a further advantage, since the entirety may be realized on a small chip, as illustrated.

With respect to the device illustrated in FIG. 2b, it is to be noted that the external nozzle 42" may optionally have a monitoring function. Regarding this, e.g., a pressure comparing sensor may be provided, configured to perform a comparison between the pressure acting in chamber 43" and the pressure acting outside of the chamber, because a throughput may be determined based on the pressure difference. According to further embodiments, the controller 35 described with respect to FIG. 1 may be integrated into the micro dosage chip. As already noted, this controller 35 may also include an integrated memory for protocolling the occurred dispensing so that the memory may subsequently be read out through a (wireless) interface. In this case, the occurring dispensing may either be established based on a detected blinking as a reaction to the free jet 26 hitting the eye or based on a detected throughput of the medication through the outlet or inlet of the micropump 20'. According to a variation, the combination of these two events, or, to be precise, the temporal event of blinking due to a dosage (throughput) is consulted as criteria for the successful dispensing.

It is further to be noted that the dosage speed is settable both via the setting deposited in the controller 35 and via the dimensioning of the elements 23', 27', 28' and, in particular, 24' as well as 42"O. The dosage speed of the free jet 26 is set so that there is no unpleasantness when the jet 26 hits the eye 12, i.e., the overpressure in the pump chamber 23' is set so that it is above the free jet limit of the micro nozzle 42"

and/or 42"O but also so that it is low enough so that the kinetic energy of the free jet 26 is not regarded as unpleasant or even damages the eye.

At this point, it is to be noted that, according to further embodiments, the monitoring of the micro dosage pump 20', in particular the monitoring of the pressure difference at the outlet of the same, may be used to identify defects, e.g., air bubbles in the chamber.

For monitoring, a Wheatstone bridge may be employed at the outlet. On the membrane comprising the outlet and/or the nozzle, four resistors arranged in a Wheatstone bridge circuit, in particular piezo-resistive resistors, are provided. Deformations of the piezo-resistive resistances and, hence, of the membrane are measured via the Wheatstone bridge circuit based on the detuning of the same, wherein, based on resistances, the throughput through the outlet/the nozzle (forward resistance with defined flow resistance) may be determined when knowing the diameter of the outlet/nozzle.

Additionally, the dosage volume per free jet 26 is adjustable both via the setting in the controller 35 and via the dimensioning of the above mentioned components. The stroke volume of the piezo actuator may be set via the design. With relatively large membrane actuators 20', e.g., with a chip size of 7×7×1 mm$^3$, the stroke volume is between 20 nanoliters and 500 nanoliters, depending on the design. With smaller membrane actuators 20', e.g., with a chip size of 3×3×1 mm$^3$, the stroke volume is between 5 nanoliters and 50 nanoliters.

According to embodiments, a free jet 26 consists of a plurality of stroke volumes dispensed shortly after one another. Assuming that the reaction time of a human being is approx. 500 ms, one has about 100 ms to dose the jet 26, before the blinking of the eye 12 leads to an incorrect dosage. When driving the actuator 28' with 50 Hz, five stroke volume packets may be ejected in 100 ms, hence, depending on the stroke volume, between five nanoliters and 2500 nanoliters, bevor the next blink follows.

A patient having to dose 2 drops of 40 µm each per eye twice daily has a daily volume consumption of 320 µl. Two reservoirs of 1 ml each would last approx. for one week. The system controller 35 detects how much was dosed and may administer the number of the necessitated jets 26.

Since the dosage accuracy is substantially larger and the incorrect dosage is much less, the active substance of the eye drops may be concentrated higher so that the volume to be doses may be reduced, further decreasing the cartridge size.

Figure 3A:
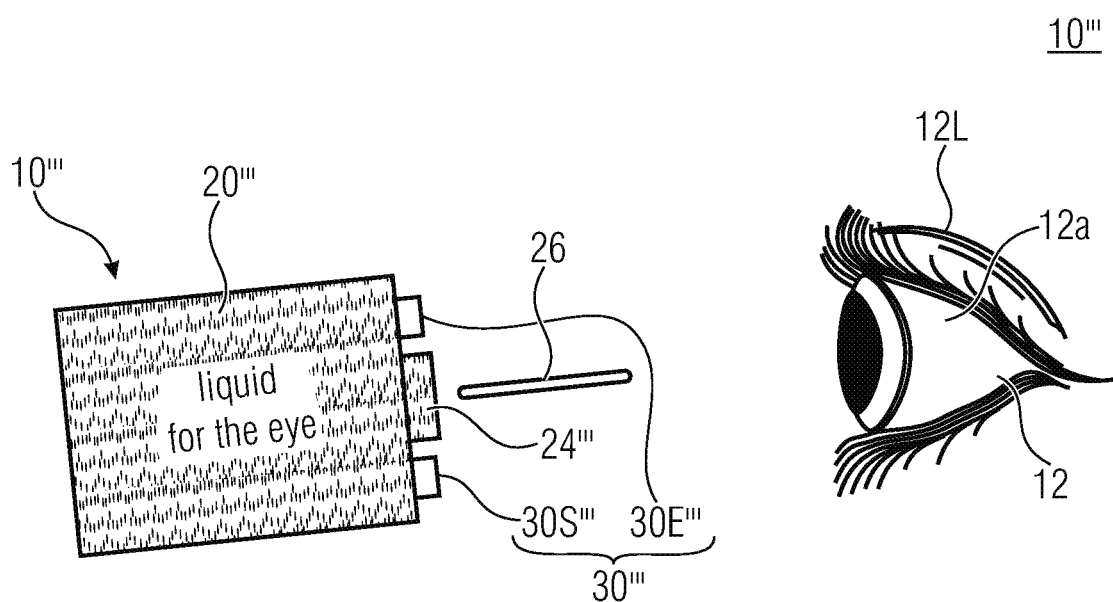
FIG. 3a shows a schematic block diagram of reflection optics of a free jet dosage system according to an embodiment.
Figure 3B:
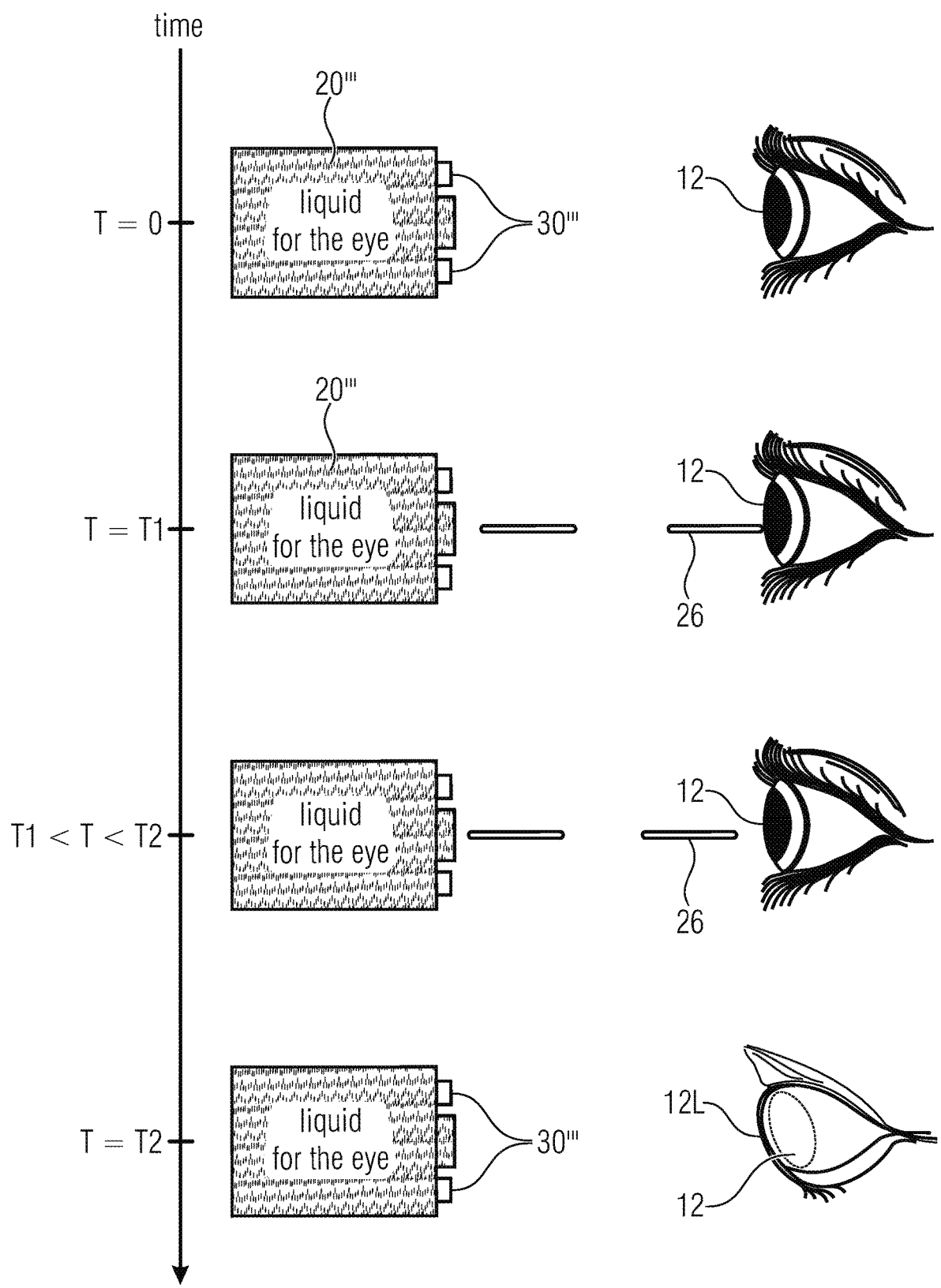
FIG. 3b shows a diagram for the instruction of the dosage monitoring means of the reflection optics.

Referring to FIGS. 3a and 3b, the reflection optics used as a sensor in the free jet dosage system is explained.

FIG. 3a shows the micro dosage system 10''' with a pump 20''' in combination with a nozzle 24''' for creating the free jet 26 to the eye. The device 10''' further includes the reflection optics 30''' consisting of a transmitter 30S''' and a receiver 30E'''. The receiver 30E''' may be a simple photocell and/or a photodiode, while the transmitter 30S''' may include a light source such as a LED. Additionally, the reflection optics 30''' may include further elements such as lenses or mirrors.

The transmitter 30S''' transmits a light ray towards the eye 12. Depending on if the light ray hits the eye ball 12a or the eyelid 12L, the reflection performance differs. As indicated by the arrow, the light ray is then reflected and hits the receiver 30E''', which is able to identify the reflection performance.

Before the exact operation including the detecting and the aid of the reflection optics 30''' and the dosing is explained based on FIG. 3b in the following, it is to be noted that the reflection optics 30''' may also include several transmitters or several receivers or combined transmitters/receivers.

FIG. 3b shows a diagram of different phases in the dosing at different points in time (T=0 to T=2) based on the micro dosage system 10'''. At the point in time T=0, the eye 12 or, more specifically, the pupil of the eye 12 is identified via the reflection optics 30''', and the micropump 20''' is activated so that the free jet 26 is dispensed towards the eye 12 at the point in time T=T1. With respect to the point in time T=0, it is further to be noted that the activation only occurs when the micro dosage pump 20''' is located in the correct position with respect to the eye 12. In other words, a position identification occurs at the point in time T=0. Now, the free jet 26 hits the eye 12 for the first time. At this point, it is to be further noted that the free jet includes several pump, or rather, conveyer operations, as indicated by the broken free jet line 26. Due to the free jet 26 hitting the eye 12, a blinking stimulus is triggered.

The point in time between T1 and T2 represents the time window for administering the liquid and is defined by the reaction time of the eye until the closure of the eyelid. Hence, the reaction time is T2−T1 (typically 100 ms).

At the point in time T=T2, the closure of the eyelid occurs, as illustrated by the closed eyelid 12L. This closure of the eyelid is identified by the reflection optics 30'''. Identifying this blinking is the so-called bio-effect. As a result of identifying the blinking, the micro dosage pump 20''' is now being deactivated so that no further free jet may be dispensed.

Optionally, when no sufficient amount has been dosed into the eye 12, the sequence may be started once more from the point in time T=0 to dose the remaining amount again.

As an alternative to the reflection optics 30''', further sensor technologies are conceivable:

Camera and image evaluation allowing for a differentiation between the left and the right eye besides the differentiation between the open and closed eye, or distance sensors, e.g., based on ultrasound.

Figure 4:
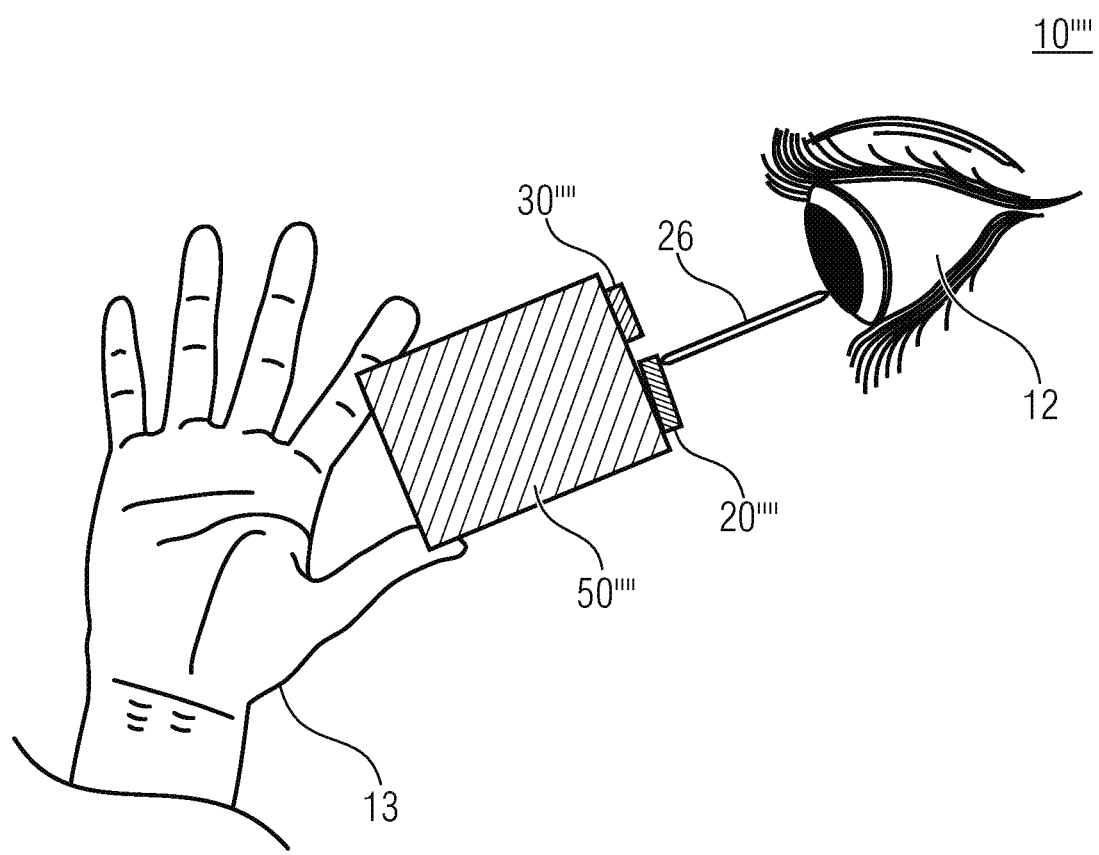
FIG. 4 shows a schematic block diagram of a free jet dosage system of the eye bottle variation according to a further embodiment.

For example, the micro dosage systems described above may be used as an eye bottle variation, as shown based on FIG. 4.

FIG. 4 shows a free jet dosage system including the dosage chip with the nozzle 20'''' and the sensor 30'''' for dispensing the fluid to the eye 12 via the free jet 26. A conventional small eye drop bottle 50'''' serves as the reservoir on which the dosage chip 20'''' and the sensor 30'''' are mounted. As explained above, the free jet 26 is dosed automatically as soon as the reservoir 50'''' and/or the free jet dosage system in general is held in the correct position with respect to the eye 12 (cf. hand 13). The concept provides the benefits that it may be mounted to and/or integrated into a conventional small eye drop bottle. In this case, the manner of operation is already present and the patients are used to the small eye drop bottles. By using simple reflection optics and simply designed dosage chips, the manufacturing costs for this variation may be kept small so that the costs of the eye drop bottle including the medication and the micro dosage device do not rise significantly compared to the simple eye drop bottle.

Even when the sensor and micropump are described as separate units in the above embodiments, in particular in the embodiment of FIG. 4, it is to be noted that the dosage chip and the sensor may obviously be conceivable as a joint element.

Figure 5:
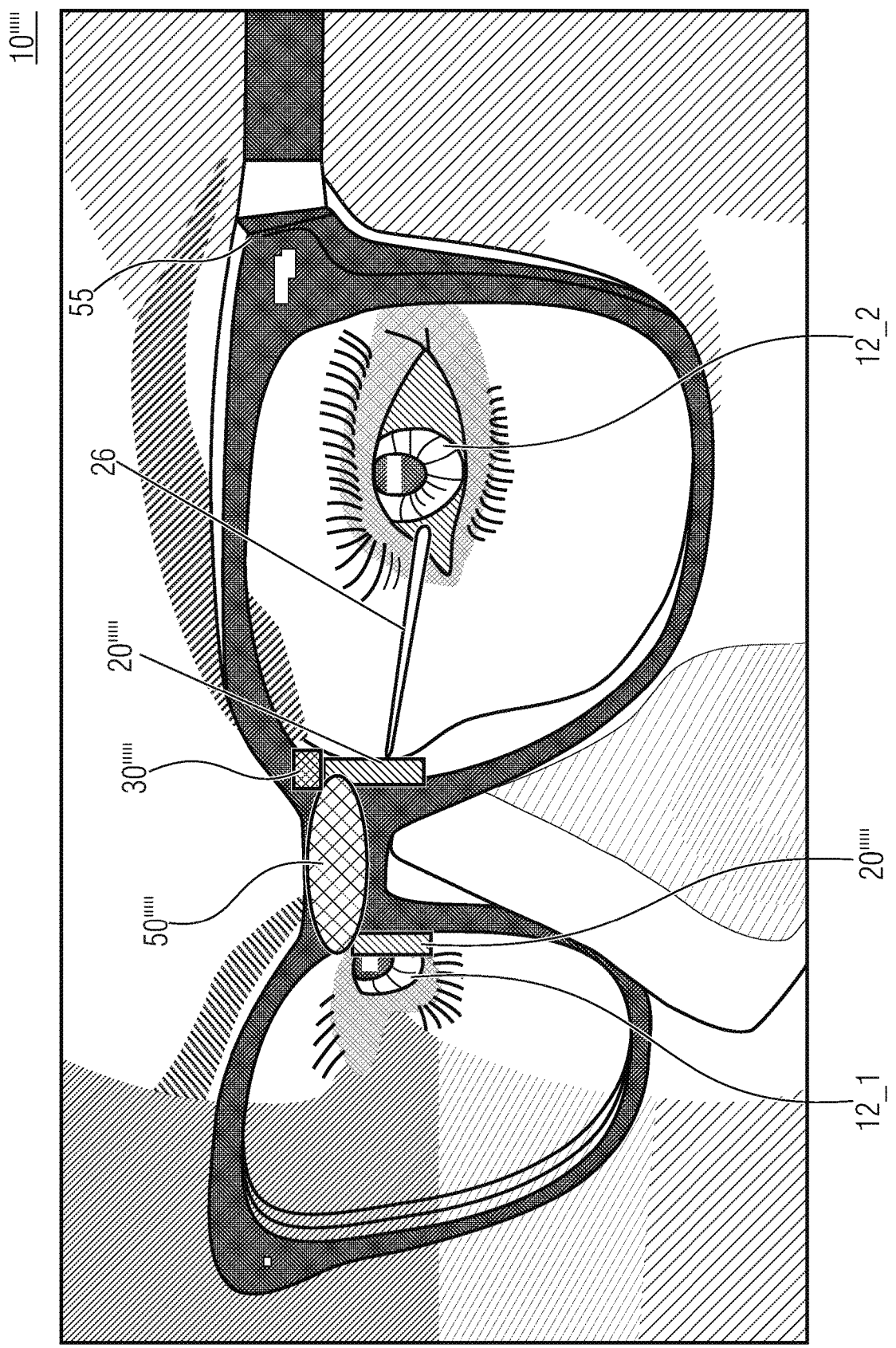
FIG. 5 shows a schematic block diagram of a free jet dosage system of the glasses variation according to an additional embodiment.

In FIG. 5, a further variation is depicted, which is an alternative to the eye drop variation. FIG. 5 shows a pair of glasses 55 with a built-in reservoir 50'''', one or, alternatively, two micro dosage chips 20'''' and one or, alternatively, two sensors 30''''.

The free jet dosage module (a combination of micropump 20'''' and nozzle chip 20''''), which may release drugs in a free jet 26 from a reservoir 50'''' to the two eyes 12_1 and 12_2 then landing in the eyes in free-flight, is mounted on the carrier 55. Additionally, a sensor system 30'''' (e.g., a camera) is installed, which may identify if the pair of glasses or the carrier 55 is placed correctly with respect to the eye 12_1 and 12_2.

The reservoir 50'''' and the free jet chip 20'''' may be exchangeable and mountable in the carrier 55 in a defined position, e.g., by clipping.

Now, a system controller (not depicted) may jet the eye drops into the eye, depending on the amount dosed by the physician. The camera serves for ensuring that the system 10'''' jets only when it is guaranteed that the jet 26 hits the eye 12_1 or 12_2.

For example, the patient may indicate the period of time in which the drops are to be administered so that he/she is not unexpectedly disturbed by a jet, e.g., during driving. For patients just using reading glasses, the glasses may automatically identify when they are being put on and then, accordingly, jet into the eye.

According to embodiments, an adjustment process would be possible which is performed after clipping the system 10'''' into the pair of glasses 55. The pair of glasses 55 is being put on, while the camera 30'''' checks if the pair of glasses sits correctly.

With respect to the reservoir 50'', 50'''' and 50'''', it is to be noted that the cartridge system may be realized. The entire system 10'''' may also be realized as a cartridge system. The background to this are hygienic reasons which, if necessitated, make it possible to replace the free jet chip and the eye drops or the eye drops reservoir, respectively, in regular intervals (e.g., once per week). For example, this may happen with a cartridge that is clipped in. The cartridge consists of an eye drop reservoir, a feeder and a free jet chip. The sensor system may be reused and does not have to be replaced or may just be added to a new system 10''''.

In conclusion, it may be noted that the free jet dosage system described above is suitable for a touch-free medication dosage, wherein the dosage occurs, e.g., out of a small eye drops bottle as a free jet.

Hence, according to a further embodiment, the micro dosage pump described above may be used without the controller and without the sensor system but in combination with ophthalmic medications. This means that a further embodiment is aimed at the use of the micro dosage pump for administering ophthalmic medications. Alternatively, as already described, the self-drawing, cost-efficient dosage chip variation may be used in connection with a simple reflection optics that identifies the right positioning of the chip towards the eye (with automatic triggering of the dosage process) and, as a success check, the unavoidable blinking (after the reaction time). With this, as explained above, the successful dosage may be logged electronically, which is then available for evaluating the compliance and monitoring the therapy. It is estimated that the manufacturing costs are less than 4 Euros with a number of units of >10 m per year. Regarding the dimensions, dosage chips (with components like a free jet system including or excluding housing, battery and/or control) may be realized in the size of $7 \times 7$ mm$^2$ or $5 \times 5$ mm$^2$ in accordance with embodiments.

Both embodiments explained above with or without control/sensor system are based on a common inventive thought with respect to the free jet dosage of ophthalmic medications. Compared to conventional dosage variations, the free jet dosage generally provides substantial advantages, such as advantages with regards to reliability of dosage, high accuracy and/or monitorability.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A free jet dosage system for administering a fluid into an eye, comprising:
    a micropump comprising an inlet and an outlet, the micropump being configured to transfer the fluid from the inlet to the outlet and to dispense the fluid at the outlet to the eye as a free jet;
    a sensor configured to sense the eye; and
    a controller for controlling the micropump configured to activate the micropump as soon as the eye is sensed by the sensor;
    wherein the sensor is configured to detect blinking of the eye, and wherein the controller is configured to determine, based on the detected blinking of the eye as a reaction within a reaction time window after the administering, that administering the fluid into the eye was successful; wherein the controller is configured to deactivate the micro dosage pump in response to the detected blinking of the eye so that no further free jet is dispensed.

2. The free jet dosage system according to claim 1, wherein the sensor comprises reflection optics configured to determine a reflectance of a surface onto which the reflection optics is directed, and to determine a surface of the eye based on the reflectance.

3. The free jet dosage system according to claim 2, wherein the reflection optics comprises a photodiode and/or a light source.

4. The free jet dosage system according to claim 1, wherein the sensor comprises an ultrasonic sensor configured to determine a distance between a surface onto which the sensor is directed and the sensor itself.

5. The free jet dosage system according to claim 1, wherein the sensor comprises a camera and/or wherein the sensor comprises a camera with evaluation electronics, the evaluation electronics being configured to determine an eye, and/or to determine if the eye is open or closed, and/or to determine if the eye is a left or a right eye.

6. The free jet dosage system according to claim 1, wherein the controller is coupled to a memory and is configured to store in the memory a successful activation of the micropump and/or successful administering of the fluid.

7. The free jet dosage system according to claim 6, wherein the memory is coupled to an interface for reading out the memory.

8. The free jet dosage system according to claim 1, wherein the sensor is configured to monitor the throughput amount at the inlet or the outlet.

9. The free jet dosage system according to claim 1, wherein the controller is configured to activate the micropump such that the fluid is administered in the appropriate amount.

10. The free jet dosage system according to claim 1, wherein the micropump is configured to dispense a maximum of 40 µl per activation.

11. The free jet dosage system according to claim 1, wherein the controller is configured to activate the micropump several times in sequence.

12. The free jet dosage system according to claim 1, wherein the micropump is self-drawing.

13. The free jet dosage system according to claim 1, wherein the micropump comprises a chamber, a membrane located in the chamber and a piezo actuator for moving the membrane, and wherein, when the piezo actuator moves the membrane, the fluid is transferred from the inlet to the outlet through the chamber.

14. The free jet dosage system according to claim 1, wherein the fluid is for treating glaucoma or dry eyes.

15. An eye drops bottle comprising a free jet dosage system according to claim 1.

16. The free jet dosage system according to claim 1, which is arranged in the frame of a pair of glasses.

17. The free jet dosage system according to claim 16, wherein the free jet dosage system is coupled to a cartridge containing the fluid.

* * * * *